United States Patent
Yokoyama et al.

(10) Patent No.: US 10,463,594 B2
(45) Date of Patent: Nov. 5, 2019

(54) COSMETIC COMPOSITION

(71) Applicant: AJINOMOTO CO., INC., Tokyo (JP)

(72) Inventors: Keiichi Yokoyama, Kawasaki (JP); Eiko Oshimura, Kawasaki (JP); Masayo Date, Kawasaki (JP); Yukiko Umezawa, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/399,347

(22) Filed: Jan. 5, 2017

(65) Prior Publication Data
US 2017/0112751 A1   Apr. 27, 2017

Related U.S. Application Data

(60) Division of application No. 14/688,575, filed on Apr. 16, 2015, which is a continuation of application No. PCT/JP2013/078152, filed on Oct. 17, 2013.

(30) Foreign Application Priority Data

Oct. 17, 2012  (JP) .................... 2012-229590

(51) Int. Cl.
| | | |
|---|---|---|
| *A61K 8/66* | (2006.01) | |
| *A61Q 5/00* | (2006.01) | |
| *A61Q 5/04* | (2006.01) | |
| *A61Q 5/06* | (2006.01) | |
| *C12N 9/80* | (2006.01) | |
| *A61Q 5/12* | (2006.01) | |
| *A61Q 19/00* | (2006.01) | |
| *A61Q 5/10* | (2006.01) | |
| *A61K 8/34* | (2006.01) | |
| *A61K 8/41* | (2006.01) | |
| *A61K 8/44* | (2006.01) | |

(52) U.S. Cl.
CPC .............. *A61K 8/66* (2013.01); *A61K 8/34* (2013.01); *A61K 8/416* (2013.01); *A61K 8/44* (2013.01); *A61Q 5/00* (2013.01); *A61Q 5/04* (2013.01); *A61Q 5/06* (2013.01); *A61Q 5/065* (2013.01); *A61Q 5/10* (2013.01); *A61Q 5/12* (2013.01); *A61Q 19/00* (2013.01); *C12N 9/80* (2013.01); *C12Y 203/02013* (2013.01); *C12Y 305/01044* (2013.01); *A61K 2800/30* (2013.01); *A61K 2800/4322* (2013.01); *C12Y 305/01* (2013.01)

(58) Field of Classification Search
CPC . A61K 8/66; A61K 8/34; A61K 8/416; A61K 8/44; A61Q 5/04; A61Q 5/06; A61Q 5/00; A61Q 5/065; A61Q 5/10; A61Q 5/12; C12Y 203/02013; C12Y 305/01044; C12N 9/90
See application file for complete search history.

(56) References Cited

U.S. PATENT DOCUMENTS

| | | | |
|---|---|---|---|
| 4,775,527 A | 10/1988 | Bires et al. | |
| 5,143,925 A | 9/1992 | Shander et al. | |
| 6,051,033 A * | 4/2000 | McDevitt ............ | D06M 13/332 435/193 |
| 8,318,223 B2 | 11/2012 | Miwa | |
| 8,709,511 B2 | 4/2014 | Yeom | |
| 2004/0072318 A1 | 4/2004 | Yamaguchi et al. | |
| 2004/0151678 A1* | 8/2004 | Barrere .................. | A61K 8/97 424/70.1 |
| 2004/0197299 A1* | 10/2004 | Delattre ................. | A61K 8/66 424/78.02 |
| 2006/0104966 A1* | 5/2006 | Green .................. | A61K 8/0208 424/94.5 |
| 2007/0116661 A1* | 5/2007 | Mata ....................... | A61K 8/36 424/70.16 |
| 2011/0064847 A1* | 3/2011 | Miwa ....................... | A23J 3/04 426/41 |
| 2012/0121760 A1* | 5/2012 | Matsunaga ............. | A21D 8/042 426/28 |
| 2012/0186596 A1 | 7/2012 | Xavier et al. | |
| 2012/0231117 A1 | 9/2012 | Timmer-Keetels | |
| 2014/0287098 A1 | 9/2014 | Rajakari | |
| 2015/0257403 A1 | 9/2015 | Sanz-Valero | |

FOREIGN PATENT DOCUMENTS

| | | |
|---|---|---|
| CN | 1091952 A | 9/1994 |
| CN | 102016057 A | 4/2011 |
| EP | 1 438 968 A1 | 7/2004 |
| JP | S62-149629 A | 7/1987 |
| JP | 1-503064 A | 10/1989 |
| JP | 3-38511 A | 2/1991 |
| JP | H07-258038 A | 10/1995 |
| JP | 8-500365 A | 1/1996 |

(Continued)

OTHER PUBLICATIONS

Yamaguchi et al., Eur. J. Biochem. 2001, 268:1410-1421.*
International Search Report dated Jan. 7, 2014 in PCT/JP2013/078152 (with English language translation).
Extended Search Report dated Mar. 3, 2016 in European Patent Application No. 13847620.5.
Combined Chinese Office Action and Search Report dated Apr. 22, 2016 in Patent Application No. 201380054137.9 (with partial English language translation and English language translation of categories of cited documents).

(Continued)

*Primary Examiner* — Robert A Wax
*Assistant Examiner* — Olga V. Tcherkasskaya
(74) *Attorney, Agent, or Firm* — Oblon, McClelland, Maier & Neustadt, L.L.P.

(57) ABSTRACT

A method for perming or coloring hair, in which hair is treated with a cosmetic composition including a protein-glutaminase and not including an alkaline substance. A method of enhancing hair-permeation of an active ingredient included in a cosmetic composition, in which a protein glutaminase is included in the cosmetic composition. The cosmetic composition does not include an alkaline substance, and the active ingredient is at least one of a hair perm agent and a hair coloring agent.

20 Claims, 2 Drawing Sheets

Specification includes a Sequence Listing.

(56) References Cited

FOREIGN PATENT DOCUMENTS

| JP | 2000-50887 A | 2/2000 |
| JP | 2004-217662 A | 8/2004 |
| JP | 2006-508766 A | 3/2006 |
| WO | WO 88/00185 A1 | 1/1988 |
| WO | WO 94/09750 A1 | 5/1994 |
| WO | WO 94/15609 A1 | 7/1994 |
| WO | WO 2006/033473 A1 | 3/2006 |
| WO | WO 2006/075771 A1 | 7/2006 |
| WO | WO 2009/113628 A1 | 9/2009 |
| WO | WO 2013/064736 A1 | 5/2013 |

OTHER PUBLICATIONS

Chinese Office Action dated Aug. 23, 2016, in Chinese Patent Application No. 201380054137.9 (with English Translation).
New chemical formulations Collection TAO JIN, p. 195, dated May 31, 2002 (English translation is incorporated in the English Translation of the Chinese Office Action dated Aug. 23, 2016 *in Chinese Patent Application No. 201380054131.9*).
Yamaguchi et al. A Novel Protein-Deamidating Enzyme from Chryseobacterium proteolyticum sp. nov., a Newly Isolated Bacterium from Soil. Appl. Environ. Microbiol 2000, 66(8): 3337-3343.
Yamaguchi et al. Protein-glutaminase from Chryseobacterium proteolyticum, an enzyme that deamidates glutaminyl residues in proteins. Purification, characterization and gene cloning. Eur. J. Biochem. 2001, 268: 1410-1421.
Japanese Notice of Reasons for Refusal dated Mar. 12, 2019, in Japanese Patent Application No. 070735/2018 (with English Translation).

* cited by examiner

COSMETIC COMPOSITION

CROSS REFERENCES TO RELATED APPLICATIONS

This application is a divisional of U.S. patent application Ser. No. 14/688,575, filed Apr. 16, 2015, which is a continuation of the International Patent Application No. PCT/JP2013/078152, filed Oct. 17, 2013, the disclosures of which are incorporated herein by reference in their entireties. This application claims priority to Japanese Application No. 2012-229590, filed Oct. 17, 2012.

TECHNICAL FIELD

The present invention relates to a cosmetic composition containing a protein-glutaminase. The present invention also relates to a protein hydrophilicity-increasing agent and a protein permeation enhancer, which contain a protein-glutaminase.

BACKGROUND ART

When a hair treatment such as perm, coloring and the like is applied, it is important to increase hydrophilicity of protein constituting the hair, namely, to swell the hair, so as to enhance permeation of a drug solution to the hair. In this way, permeation of chemicals such as a perming agent, a hair color and the like is facilitated. A hair swelling treatment is mostly performed using an alkaline substance such as ammonia, monoethanolamine and the like (e.g., JP-A-1-503064). By doing so, the alkaline substance acts on the hair to ionize polar groups in protein in the hair, and induces structural changes. However, such hair treatment using an alkaline substance simultaneously causes side effects such as hydrolysis of protein, loss of lipid and the like in the hair, and consequently damages hair and induces skin irritation.

On the other hand, it is important to permeate an active ingredient contained in a cosmetic or a skin external preparation to hair or skin and enhance the permeation, thereby to increase the effect of the active ingredient. For this end, various permeation enhancers have conventionally been used. As such permeation enhancer, dimethyl sulfoxide, oleic acid, benzyl alcohol and the like are known (e.g., JP-A-8-500365). However, such permeation enhancers simultaneously have problems of skin irritation and the like, and are insufficient in terms of safety. Also, the sensory feel thereof is not good. Therefore, conventional permeation enhancers are not sufficiently satisfactory for users.

SUMMARY OF THE INVENTION

Problems to be Solved by the Invention

The present invention aims to provide a cosmetic composition having a superior protein hydrophilicity-increasing effect and a superior permeability enhancing effect, while suppressing hair damage and skin irritation. The present invention also aims to provide an agent having a superior protein hydrophilicity-increasing effect and a superior permeability enhancing effect.

Means of Solving the Problems

The present inventors have conducted intensive studies of the aforementioned problems and found that protein-glutaminase increases hydrophilicity of proteins in tissues, can particularly swell hair, skin and the like, and does not easily damage hair, skin and the like. Furthermore, the present inventors have further found that protein-glutaminase effectively enhances permeation of the active ingredient contained in cosmetics or skin external preparations to hair and skin. Based on these findings, the present inventors have further studied and completed the present invention.

Accordingly, the present invention relates to the following.

[1] A cosmetic composition comprising a protein-glutaminase.
[2] The cosmetic composition of [1], wherein the protein-glutaminase has a molecular weight of 10-40 kDa.
[3] The cosmetic composition of [1] or [2], wherein the content of the protein-glutaminase is 0.00001-10 mass %.
[4] The cosmetic composition of any of [1]-[3], wherein the protein-glutaminase is derived from a bacterium belonging to the genus *Chryseobacterium*.
[5] The cosmetic composition of any of [1]-[4], further comprising transglutaminase.
[6] The cosmetic composition of [5], wherein the content of the transglutaminase is 0.001-2 mass %.
[7] The cosmetic composition of [5] or [6], wherein a mixing ratio of the protein-glutaminase and transglutaminase (protein-glutaminase:transglutaminase (mass:mass)) is 1:1-1:10000.
[8] The cosmetic composition of any of [1]-[7], further comprising amino acid, acylamino acid, acylamino acid ester, acylamino acid amide, peptide, acylpeptide or a salt thereof.
[9] The cosmetic composition of [8], wherein a content of the amino acid, acylamino acid, acylamino acid ester, acylamino acid amide, peptide, acylpeptide or a salt thereof is 0.005-50 mass %.
[10] The cosmetic composition of any of [1]-[9], further comprising alcohol.
[11] The cosmetic composition of [10], wherein a content of the alcohol is 0.005-50 mass %.
[12] The cosmetic composition of [10] or [11], wherein the alcohol is saturated or unsaturated monovalent $C_{1-6}$ alcohol or polyvalent alcohol.
[13] The cosmetic composition of any of [1]-[12], which is a skin cosmetic.
[14] The cosmetic composition of any of [1]-[12], which is a hair cosmetic.
[15] The cosmetic composition of [14], wherein the hair cosmetic is a perming agent or a hair color.
[16] An agent for increasing hydrophilicity of a protein, which comprises a protein-glutaminase.
[17] Use of a protein-glutaminase in increasing hydrophilicity of a protein.
[18] A permeation enhancer comprising a protein-glutaminase.
[19] Use of a protein-glutaminase in enhancing permeation of an active ingredient.
[20] The use of [19], wherein the active ingredient is transglutaminase.
[21] The use of [19], wherein the active ingredient is amino acid, acylamino acid, acylamino acid ester, acylamino acid amide, peptide, acylpeptide or a salt thereof.

Effect of the Invention

According to the present invention, static electrical repulsion increases in molecules of the protein in hair, skin and the like, whereby they become swollen, as a result of which permeability of the active ingredient contained in a cosmetic or skin external preparation to the hair, skin and the like is increased. Moreover, hydrophilicity of the protein can be increased without damaging hair, skin and the like, or causing skin irritation, and the hair, skin and the like can be effectively swollen.

According to the present invention, moreover, an agent that increases hydrophilicity of protein in tissues (e.g., hair, skin etc.) is provided. Furthermore, an agent that enhances permeation of an active ingredient contained in a cosmetic or skin external preparation to tissues (e.g., hair, skin etc.) is provided. All these agents can be utilized not only for cosmetics but also medicaments such as skin external preparation, transdermal absorption preparation and the like.

DESCRIPTION OF EMBODIMENTS

Figure 1:
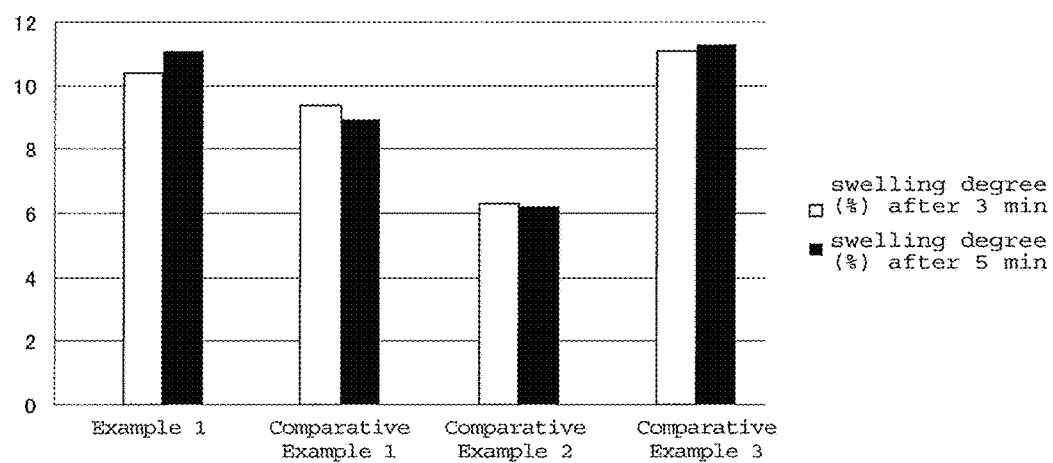
FIG. 1 is a graph showing the swelling degree of hair when treated with various samples, wherein the vertical axis of the graph shows swelling degree (%) of hair, and the horizontal axis shows the kind of the sample and treatment time (3 min and 5 min).

While the protein-glutaminase in the present invention is not particularly limited, for example, those shown by EC number (Enzyme Commission No.) of EC3.5.1 (or EC3.5.1.X (X is any number, for example, 44 etc.)) can be used. Not being particularly limited, as the protein-glutaminase in the present invention, those derived from microorganisms can be used. Examples of the microorganism include bacteria belonging to the genus *Chryseobacterium* and the like. Of those, bacteria named *Chryseobacterium proteolyticum, Chryseobacterium gleum* are preferable. As the *Chryseobacterium proteolyticum* strain, various strains can be used as long as they can afford the effect of the present invention and, for example, strain 9670 and the like can be mentioned. These microorganisms are easily available from a depositary institution and the like. For example, *Chryseobacterium proteolyticum* strain 9670 is deposited at the National Institute of Advanced Industrial Science and Technology, the International Patent Organism Depositary (305-8566 Tsukuba Central 6, 1-1, Higashi 1-Chome Tsukuba-shi, Ibaraki-ken) under accession number FERM BP-7351, as described in JP-A-2005-52158.

The protein-glutaminase derived from *Chryseobacterium proteolyticum* strain 9670 is a single strand polypeptide composed of full-length 320 amino acids, and the amino acid sequence thereof is registered as Genbank Accession No. BAB21508 (SEQ ID NO: 2). Also, a base sequence encoding the polypeptide is registered as Genbank Accession No. AB046594 (SEQ ID NO: 1).

The above-mentioned polypeptide is encoded as a preproform, wherein 135 residues on the N terminal side is a preproregion and the remaining 185 residues correspond to a mature form. The amino acid sequence of the mature form is shown in SEQ ID NO: 4, and the base sequence encoding same is shown in SEQ ID NO: 3. Therefore, the protein-glutaminase in the present invention can be said, for example, a polypeptide containing an amino acid sequence the same or substantially the same as the amino acid sequence shown in SEQ ID NO: 4. Of the 135 residues in the above-mentioned preproregion, since 21 residues on the N terminal side have the characteristics of a signal sequence, they are assumed to form a pre-region, and the remaining 114 residues are assumed to form a pro-region.

As an amino acid sequence substantially the same as the amino acid shown in sequence SEQ ID NO: 4, an amino acid sequence having identity of not less than 50%, preferably not less than 60%, more preferably not less than 70%, further preferably not less than 80%, further more preferably not less than 90%, particularly preferably not less than 95%, most preferably not less than 99%, with the amino acid sequence shown in SEQ ID NO: 4 can be mentioned. The "identity" here means a ratio (%) of identical amino acids to all overlapping amino acid residues in the optimal alignment where two amino acid sequences are aligned using a mathematical algorithm known in the technical field.

Examples of the amino acid sequence substantially the same as the amino acid sequence shown in SEQ ID NO: 4 include (1) an amino acid sequence which is the amino acid sequence shown in SEQ ID NO: 4 wherein one or more (preferably, about 1-30, more preferably about 1-10, further preferably 1 or 2) amino acids are deleted, (2) an amino acid sequence which is the amino acid sequence shown in SEQ ID NO: 4 wherein one or more (preferably, about 1-30, more preferably about 1-10, further preferably 1 or 2) amino acids are added, (3) an amino acid sequence which is the amino acid sequence shown in SEQ ID NO: 4 wherein one or more (preferably, about 1-30, more preferably about 1-10, further preferably 1 or 2) amino acids are inserted, (4) an amino acid sequence which is the amino acid sequence shown in SEQ ID NO: 4 wherein one or more (preferably, about 1-30, more preferably about 1-10, further preferably 1 or 2) amino acids are substituted by other amino acids, and (5) an amino acid sequence combining them and the like.

When the amino acid sequence is inserted, deleted, added or substituted as mentioned above, the position of insertion, deletion, addition or substitution is not particularly limited as long as a polypeptide having such amino acid sequence affords the effect of the present invention.

While the length of the protein-glutaminase is not particularly limited as long as the effect of the present invention is afforded, it is, for example, not more than 400 amino acids, preferably not more than 300 amino acids, more preferably not more than 200 amino acids, from the aspects of easy preparation and stability of polypeptide.

The production method of the protein-glutaminase is not particularly limited, and can be produced by a known method. For example, it can be obtained by subjecting a bacterium of the genus *Chryseobacterium* (e.g., *Chryseobacterium proteolyticum* strain 9670) to liquid culture (e.g., in LB medium at 25° C. for 40 hr), and subjecting the obtained culture medium to sterile filtration, desalting and concentration by ultrafiltration, and purification by ion exchange chromatography. The methods and conditions for filtration and ion exchange chromatography can be appropriately selected by a technique known per se. Other than the above, a method including introducing a gene encoding a protein-glutaminase (e.g., polynucleotide sequence shown in SEQ ID NO: 1 or 3) into a host such as *E. coli, Corynebacterium* and the like to allow for expression of the protein-glutaminase in the host, and isolating and purifying same can also be utilized. The method utilizing the gene can be performed according to the method described in, for example, Y. Kikuchi et al., Applied microbiology and biotechnology 78, 67-74 (2008), or S. Yamaguchi et al., Eur. J. Biochem. 268, 1410-1421 (2001). As protein-glutaminase, a commercially available product can also be used.

While the molecular weight of the protein-glutaminase in the present invention is not particularly limited as long as the molecule has the activity of protein-glutaminase, it is preferably 1-200 kDa, more preferably 5-100 kDa, further preferably 10-60 kDa, further more preferably 10-40 kDa. The molecular weight can be calculated from the amino acid sequence, or can also be measured using SDS polyacrylamide gel electrophoresis and the like. SDS-polyacrylamide gel electrophoresis can be performed by a method known per se. The activity of protein-glutaminase can be measured using N-carbobenzoxy-L-glutamyl-glycine (N-carbobenzoxy-L-glutamyl-glycine) (CBZ-Gln-Gly) as a substrate, and measuring the amount of ammonia produced by the reaction with a protein-glutaminase (e.g., S. Yamaguchi et al. Appl. Environ. Microbiol. 66, 3337-3343 (2000)). CBZ-Gln-Gly to be used as a substrate may be produced by a method known per se, or may be a commercially available product, or its production may be committed to an outside manufacture and the like.

In the present invention, the above-mentioned protein-glutaminase is contained in a cosmetic composition. While the content of the protein-glutaminase in the cosmetic composition of the present invention varies depending on the form, use frequency and treatment time of the preparation, titer of the protein-glutaminase and the like, it is preferably not less than 0.00001 mass %, more preferably not less than 0.00005 mass %, further preferably not less than 0.0001 mass %. The content is preferably not more than 10 mass %, more preferably not more than 5 mass %, further preferably not more than 2 mass %.

The cosmetic composition of the present invention preferably further contains, for example, transglutaminase as an active ingredient. Transglutaminase is one of the protein-modifying enzymes, and has an action to catalyze a reaction between a γ-carboxylamide group of a glutamine residue and a ε-amino group of a lysine residue in a protein or peptide, and catalyze a crosslinking formation reaction via a ε-(γ-glutamyl)lysine bond. In hair, for example, transglutaminase itself catalyzes a reaction between a free glutamine residue and a lysine residue mainly present in the hair outermost layer and forms a crosslink comprising a ε-(γ-glutamyl) lysine bond as mentioned above, thus densifying the surface structure of the hair, improving damage hair, promoting water retaining function, improving hair moisture retaining property and further exhibiting a damage hair improving effect to impart glossiness, flexibility and elasticity to the hair. In the present invention, by further combining the above-mentioned protein-glutaminase for, for example, hair, the hair is essentially improved and the strength (particularly, tensile strength) of the hair can be effectively increased.

While transglutaminase in the present invention is not particularly limited, for example, one having an EC number (Enzyme Commission No.) of EC2.3.2.13 can be used. Transglutaminase is mainly present in various tissues and blood cells of animals. Therefore, transglutaminase used in the present invention can be isolated and purified from the liver, serum, platelet, epidermis and the like of mammals such as human, mouse, rat, guinea pig, swine, bovine, sheep and the like by a method known per se. In the present invention, moreover, not only transglutaminase derived from an animal but also, for example, transglutaminase derived from a microorganism such as *Streptomyces mobaraensis* and the like and plant-derived transglutaminase can be used irrespective of the origin thereof. As transglutaminase, a commercially available product can be preferably used, which can be obtained with ease, since it is commercially available widely in the field of, for example, food and the like. Transglutaminase to be used in the present invention may be produced by a genetic recombination method.

While transglutaminase generally requires calcium ion for its reaction, calcium ion-independent transglutaminase is also present depending on the kind (e.g., JP-A-1-27471 etc.). Therefore, calcium ion may be added to the composition of the present invention where necessary, though not essentially. Examples of the compound capable of supplying calcium ion in the present invention include calcium chloride, calcium sulfate, and calcium bromide and the like. Of these, calcium chloride is preferable. The amount thereof to be added is generally 1-20 mM, preferably 3-10 mM, in calcium concentration.

While the molecular weight of the transglutaminase in the present invention is not particularly limited as long as the molecule has the activity of transglutaminase, it is preferably 1-200 kDa, more preferably 5-100 kDa, further preferably 10-80 kDa, and further more preferably 30-60 kDa. The molecular weight can be measured by SDS-polyacrylamide gel electrophoresis. SDS-polyacrylamide gel electrophoresis can be performed by a method known per se. The activity of transglutaminase can be measured by reacting same with benzyloxycarbonyl-L-glutamyl-glycine and hydroxylamine as substrates, with the addition of a necessary amount of calcium ion when calcium ion is needed, forming an iron complex of the produced hydroxamic acid in the presence of trichloroacetic acid, measuring the absorbance at 525 nm, and calculating the amount of hydroxamic acid from an analytical curve thereof.

While the content of transglutaminase in the cosmetic composition of the present invention varies depending on the form, use frequency and treatment time of the preparation, titer of transglutaminase and the like, it is preferably not less than 0.001 mass %, more preferably not less than 0.01 mass %, further preferably not less than 0.02 mass %. The content is preferably not more than 2 mass %, more preferably not more than 1 mass %, further preferably not more than 0.5 mass %. When transglutaminase is contained in the above-mentioned ranges, it can effectively improve the strength of the hair in combination with a protein-glutaminase.

In the cosmetic composition of the present invention, the mixing ratio of the protein-glutaminase and transglutaminase (protein-glutaminase:transglutaminase (mass:mass)) is not necessarily limited by the titer and the like of the both enzymes; however, it is preferably 1:1-1:10000, more preferably 1:2-1:1000, further preferably 1:10-1:100. When the mixing ratio of the both enzymes is within the above-mentioned ranges, the effect of the combined use of the protein-glutaminase and transglutaminase becomes higher, which can contribute to a remarkable improvement of the hair strength.

In another embodiment, the cosmetic composition of the present invention preferably further contains, for example, amino acid or a salt thereof, acylamino acid, an ester or amide thereof, or a salt thereof, peptide or a salt thereof, acylpeptide or a salt thereof as an active ingredient. Only one kind of these may be used, or two or more kinds thereof may be used in combination.

Examples of the amino acid include arginine, lysine, glutamic acid, aspartic acid, valine, leucine, isoleucine, serine, glycine, alanine, proline, hydroxyproline, threonine, histidine, phenylalanine, tryptophan, tyrosine, glutamine, asparagine, cysteine, cystine, pyrrolidone carboxylic acid, and methionine.

While acylamino acid is not particularly limited, acylamino acid obtained by acylating the same amino acid as those exemplified above can be mentioned. The acyl group of acylamino acid and acylpeptide is, for example, an acyl group induced from saturated or unsaturated fatty acid having 2-23 carbon atoms, and concrete examples thereof include acetyl group, propanoyl group, isopropanoyl group, butanoyl group, isobutanoyl group, sec-butanoyl group, tert-butanoyl group, pentanoyl group, isopentanoyl group, sec-pentanoyl group, tert-pentanoyl group, hexanoyl group, heptanoyl group, octanoyl group, tert-octanoyl group, 2-ethylhexanoyl group, nonanoyl group, isononanoyl group, decanoyl group, isodecanoyl group, undecanoyl group, lauroyl group, myristoyl group, palmitoyl group, stearoyl group, behenoyl group, undecylenoyl group and oleoyl group and the like. It may be an acyl group induced from a single composition acid, or an acyl group induced from naturally obtained mixed fatty acid such as coconut oil fatty acid, castor oil fatty acid, olive oil fatty acid, palm oil fatty acid and the like or synthetically obtained fatty acid (including branched fatty acid). One kind of these may be used, or two or more kinds thereof may be used in a mixture. It is preferably an acyl group induced from saturated or unsaturated fatty acid having 2-18 carbon atoms, more preferably an acyl group induced from saturated or unsaturated fatty acid having 2-12 carbon atoms, further preferably an acyl group induced from saturated or unsaturated fatty acid having 2-6 carbon atoms. An acyl group induced from saturated fatty acid is more preferable than an acyl group induced from unsaturated fatty acid.

As the ester group of acylamino acid ester, alkyl ester or aralkyl ester can be mentioned and, for example, an ester having a $C_{1-24}$ alkyl group or $C_{1-24}$ alkenyl group can be mentioned, with preference given to an alkyl ester having a $C_{1-6}$ alkyl group.

Examples of the $C_{1-24}$ alkyl group include methyl, ethyl, propyl, isopropyl, butyl, isobutyl, sec-butyl, tert-butyl, pentyl, isopentyl, sec-pentyl, neopentyl, tert-pentyl, hexyl, sec-hexyl, heptyl, sec-heptyl, octyl, 2-ethylhexyl, sec-octyl, nonyl, sec-nonyl, decyl, sec-decyl, undecyl, sec-undecyl, dodecyl, sec-dodecyl, tridecyl, isotridecyl, sec-tridecyl, tetradecyl, sec-tetradecyl, hexadecyl, sec-hexadecyl, stearyl, monomethyl branched-isostearyl, icosyl, docosyl, tetracosyl, triacontyl, 2-butyloctyl, 2-hexyloctyl, 2-butyldecyl, 2-hexyldecyl, 2-octyldecyl, 2-hexyldodecyl, 2-octyldodecyl, 2-decyldodecyl, 2-octyltetradecyl, 2-decyltetradecyl, 2-dodecyltetradecyl, 2-decylhexadecyl, 2-dodecylhexadecyl, 2-tetradecylhexadecyl, 2-dodecyloctadecyl, 2-tetradecyloctadecyl, 2-hexadecyloctadecyl, 2-tetradecylicosyl, 2-hexadecylicosyl, and 2-octadecylicosyl and the like.

Particular examples of the $C_{1-6}$ alkyl group include methyl, ethyl, isopropyl, propyl, butyl, isobutyl, sec-butyl, tert-butyl, pentyl, sec-pentyl, tert-pentyl, isopentyl, and hexyl.

Examples of the $C_{1-24}$ alkenyl group include vinyl, allyl, propenyl, isopropenyl, butenyl, isobutenyl, pentenyl, isopentenyl, hexenyl, heptenyl, octenyl, nonenyl, decenyl, undecenyl, dodecenyl, tetradecenyl, oleyl, linoleyl and the like.

As the amide group of acylamino acid amide, alkylamide and aralkylamide can be mentioned and, for example, amide having a $C_{1-24}$ alkyl group or $C_{1-24}$ alkenyl group can be mentioned, with preference given to alkylamide having a $C_{1-6}$ alkyl group.

As peptide, dipeptide, tripeptide or tetrapeptide composed of one or more kinds of the amino acids recited above as examples is preferable. In the present invention, it is more preferably tripeptide, particularly preferably glycylglycylglycine (Gly-Gly-Gly).

While the content of the above-mentioned amino acid or a salt thereof, acylamino acid, an ester or amide thereof, or a salt thereof, peptide or a salt thereof, acylpeptide or a salt thereof in the cosmetic composition of the present invention varies depending on the form, use frequency, treatment time, kind etc. of the preparation, it is preferably not less than 0.005 mass %, more preferably not less than 0.01 mass %, further preferably not less than 0.1 mass %. The content is preferably not more than 50 mass %, more preferably not more than 30 mass %, further preferably not more than 20 mass %.

The cosmetic composition of the present invention preferably further contains alcohol in addition to the above-mentioned various ingredients. When alcohol is contained, the permeability of enzyme increases, and the enzyme reaction proceeds more effectively. Consequently, for example, improvement of damage hair, promotion of water retaining function, improvement of hair moisture retaining property, and improvement of damage hair improvement effect that produces glossiness, flexibility and elasticity of the hair are expected.

The alcohol to be contained in the cosmetic composition of the present invention is not particularly limited and, for example, saturated or unsaturated monovalent $C_{1-6}$ alcohol, saturated or unsaturated monovalent $C_{8-38}$ alcohol, and polyvalent alcohol can be mentioned.

Examples of the saturated or unsaturated monovalent $C_{1-6}$ alcohol include ethanol, propanol, isopropanol, butanol and the like.

Examples of the saturated or unsaturated monovalent $C_{8-38}$ alcohol include straight chain saturated alcohols such as capryl alcohol, lauryl alcohol, myristyl alcohol, cetyl alcohol, stearyl alcohol, arachidyl alcohol, behenyl alcohol and the like; branched chain saturated alcohols such as 2-hexyldecyl alcohol, 2-octyldodecyl alcohol, isostearyl alcohol, decyltetradecyl alcohol and the like; straight chain unsaturated alcohols such as oleyl alcohol, linoleyl alcohol and the like; and the like.

Examples of the polyvalent alcohol include divalent alcohols such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, 1,2-hexanediol, hexylene glycol, octylene glycol and the like; trivalent alcohols such as glycerin, trimethylolpropane, 1,2,6-hexanetriol and the like; tetravalent alcohols such as pentaerythritol and the like; pentavalent alcohols such as xylitol and the like; hexavalent alcohols such as sorbitol, mannitol and the like; polyvalent alcohol copolymers such as diethylene glycol, dipropylene glycol, triethylene glycol, polypropylene glycol, triglycerin, tetraglycerin, polyglycerin and the like; divalent alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether and the like; divalent alcohol alkyl ethers such as diethylene glycol monomethyl ether, diethylene glycol monoethyl ether, diethylene glycol monobutyl ether, diethylene glycol, dimethyl ether, diethylene glycol diethyl ether, diethylene glycol dibutyl ether, diethylene glycol methylethyl ether, triethylene glycol monomethyl ether, triethylene glycol monoethyl ether, triethylene glycol monoethyl ether, propylene glycol monomethyl ether, propylene glycol monoethyl ether, propylene glycol monobutyl ether, propylene glycol monoisopropyl ether, dipropylene glycol methyl ether, dipropylene glycol ethyl ether, dipropylene glycol butyl ether and the like; divalent alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, ethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate and the like; glycerin monoalkyl ethers such as chimyl alcohol, selachyl alcohol, batyl alcohol and the like; sugar alcohols such as sorbitol, maltitol, mannitol, erythritol, xylitol, starch-decomposed sugar reduced alcohol and the like; glysolid, tetrahydrofurfuryl alcohol, POE-tetrahydrofurfuryl alcohol, POP-butyl ether, POP-POE-butyl ether, tripolyoxypropylene glyceryl ether, POP-glyceryl ether, POP-glyceryl ether phosphate, POP-POE pentaerythritol ether and the like.

Only one kind of alcohol exemplified above can be used, or two or more kinds thereof can be used in combination. Of the exemplified alcohols, preferred is saturated or unsaturated monovalent $C_{1-6}$ alcohol or polyvalent alcohol, more preferred is ethanol, propanol, ethylene glycol, propylene glycol, 1,2-butylene glycol, 1,3-butylene glycol or 1,2-hexanediol, further preferred is ethanol or 1,2-hexanediol from the aspects of the effect of the present invention.

While the content of the alcohol in the cosmetic composition of the present invention varies depending on the form, use frequency and treatment time of the preparation, the kind of alcohol to be used and the like, it is preferably not less than 0.005 mass %, more preferably not less than 0.01 mass %, further preferably not less than 0.1 mass %. The content is preferably not more than 50 mass %, more preferably not more than 30 mass %, further preferably not more than 20 mass %. When alcohol is contained within the above-mentioned ranges, the permeability of enzyme increases, and the enzyme reaction proceeds more effectively. Consequently, for example, improvement of damage hair, promotion of water retaining function, improvement of hair moisture retaining property, and improvement of damage hair improvement effect that produces glossiness, flexibility and elasticity of the hair are expected.

The pH of the cosmetic composition of the present invention is not particularly limited as long as the effect of the present invention is not inhibited. The pH of the cosmetic composition of the present invention is preferably 2.5-10.0, preferably 3.0-9.0, more preferably 4.0-7.5.

The cosmetic composition of the present invention can further contain, in addition to the above-mentioned ingredients, for example, an efficacy ingredient conventionally used for cosmetics. While the efficacy ingredient is not particularly limited, whitening agents, ingredients capable of maintaining the health of hair or ingredients capable of enhancing hair growth such as hair-growth drugs, conditioners and the like, and the like are preferable.

Examples of the whitening agent include hydroquinones and derivatives thereof such as hydroquinone, arbutin and the like; ascorbic acid and derivatives thereof such as ascorbic acid, sodium ascorbate, sodium ascorbate sulfate, ascorbic acid phosphate magnesium salt, ascorbic acid phosphate sodium salt, ascorbic acid glucoside, vitamin C ethyl and the like; plant extracts; polyphenols such as ellagic acid, gallic acid, pentagalloyl glucose, resveratrol, and the like.

Examples of the hair-growth drug include pantothenic acid and derivatives thereof, allantoin, biotin, mononitro guaiacol, adenosine, pentadecanoic acid glyceride, dialkyl monoamine derivative, coleus extract, chlorophyll, photosensitizer, estradiol, ethynylestradiol, pyridoxine hydrochloride, thioxolone, sulfur, organic sulfur substance and the like. The content of various efficacy ingredients in the cosmetic composition of the present invention can be appropriately determined, according to the kind and the like of the efficacy ingredients, to fall within the range that does not inhibit the effect of the present invention.

The cosmetic composition of the present invention can further contain other ingredients such as oil, surfactant, moisturizer, thickener, antioxidant, chelating agent, pH adjuster, preservative, flavor, dye and the like. The specific kind and content of these ingredients can be appropriately determined according to the object thereof and the like, as long as the effect of the present invention is not inhibited.

The cosmetic composition of the present invention can be produced according to a conventional method, and can be, for example, any form of preparation applicable to hair, skin and the like. The composition is not particularly limited and can take any form such as liquid, cream, gel, paste and the like. The composition in the form of a liquid can be filled in a pressure tight case as necessary, in combination with, for example, carbon dioxide gas, oxygen gas, LPG and the like, and can also be used as a propellant. The appearance of the protein hydrophilicity-increasing agent of the present invention is not particularly limited, and can be any appropriate appearance, for example, transparent, white turbid, pearl-like and the like.

The cosmetic composition of the present invention is not particularly limited, and specific examples thereof include hair cosmetics, such as perming agent, hair color, hair-growth medicine, hair-growth drug, hair cream, hair lotion, hair serum, hair milk, hair ointment, hair treatment, hair conditioner, shampoo, rinse and the like, skin cosmetics such as facial wash, skin lotion, skin milk, cream, gel, serum, facial mask, mask, soap, body shampoo, face powder, foundation, lip color, blush, eyeliner, mascara, eye shadow, eyebrow pencil and the like, and the like.

The effects of the cosmetic composition of the present invention explained above are attributable to the action specific to protein-glutaminase that the hydrophilicity of protein in a tissue (e.g., hair, skin etc.) can be improved without damaging the tissue. This is assumed to be because protein-glutaminase probably has an action to convert a glutamine residue in a protein or peptide to a glutamic acid residue, and the conversion of amino acid is performed without cleaving the peptide bond in the protein or peptide. Thus, protein-glutaminase is useful since it increases hydrophilicity of protein in a tissue. Accordingly, the present invention further provides a protein hydrophilicity-increasing agent containing a protein-glutaminase. The protein of the "protein hydrophilicity-increasing agent" of the present invention means a protein constituting hair, skin, nail and the like of human.

With the protein hydrophilicity-increasing effect, permeation of an active ingredient contained in the composition to a tissue (e.g., hair, skin etc.) can be enhanced. Therefore, the present invention further provides an (active ingredient) permeation enhancer containing a protein-glutaminase. The above-mentioned protein hydrophilicity-increasing agent and the permeation enhancer are collectively referred hereafter to as "the agent of the present invention".

The agent of the present invention is useful not only as a cosmetic but also as a medicament, where the application target is mammal (e.g., human, mouse, rat, hamster, rabbit, cat, dog, bovine, sheep, monkey etc.). The application target of the agent of the present invention is preferably human. For application to a mammal other than human, the dose of the agent of the present invention can be appropriately reduced according to the body weight or size of the animal.

When the agent of the present invention is used as a medicament, the administration method thereof is not particularly limited; however, parenteral administration is preferable and transdermal administration is particularly preferable from the aspects of the effect thereof.

While the dosage form of the agent of the present invention is not particularly limited, it is preferably external preparation (e.g., external solid agent (external powder etc.), external liquid (liniment, lotion etc.), spray (external aerosol, pump spray etc.), ointment, cream, gel, adhesive preparation (tape, cataplasm etc.) and the like). The agent of the present invention can be produced by a method conventionally used in the technical field of preparation formulation, for example, the method described in the Japanese Pharmacopoeia and the like.

The agent of the present invention may be the above-mentioned protein-glutaminase itself, or formulated by blending with an appropriate pharmaceutically acceptable carrier, when necessary for formulation. While the pharmaceutically acceptable carrier is not particularly limited, for example, aqueous carrier, milky carrier, gel-like carrier, cream base, ointment base and the like can be mentioned. Specific examples thereof include oily ingredients such as animal and vegetable fats and oils, waxes, fatty acid, aliphatic alcohol, ester oils, hydrocarbon oils, silicone oils and the like; surfactants such as nonionic surfactant, anionic surfactant, amphoteric surfactant, cationic surfactant and the like; lower alcohols such as ethanol and the like; polyvalent alcohols such as glycerin, 1,3-butanediol and the like; thickeners such as carboxyvinyl polymer, hydroxycellulose and the like; pH adjusters such as lactic acid and a salt thereof, citric acid and a salt thereof and the like; bases such as potassium hydroxide, sodium hydroxide, L-arginine and the like; antioxidants such as tocopherol and a derivative thereof and the like; UV inhibitor, antimicrobial/antifungal agent, flavor, dye, pigment and the like, ingredients generally used in the medicament field and the like.

The content of protein-glutaminase in the agent of the present invention when formulated using a carrier is not particularly limited, and can be appropriately adjusted to contain protein-glutaminase in an amount necessary for affording the effect of the present invention. While the content of protein-glutaminase varies depending on the kind of the dosage form and the kind of the carrier to be used, it is, for example, 0.1-30 mass %, preferably 0.5-20 mass %, more preferably 1-20 mass %, further preferably 1-10 mass %.

While the dose of the agent of the present invention varies depending on the subject of administration, target organ, symptom, administration method and the like, when it is parenterally administered to human, for example, the mass of protein-glutaminase for an adult (body weight 60 kg) is about 0.01-10 mg, preferably about 0.1-5 mg, more preferably 1-4 mg, per day. When the subject of administration is other than human, an amount based on that for body weight 60 kg can be administered. Alternatively, an appropriate dose may be set for the subject of administration. In the present invention, the above-mentioned daily dose can be administered once or in 2-4, preferably 2-3, portions as necessary at appropriate intervals.

The agent of the present invention can be used in combination with, for example, the aforementioned transglutaminase, amino acid or a salt thereof, acylamino acid, an ester or amide thereof, or a salt thereof, peptide or a salt thereof, acylpeptide or a salt thereof, alcohol, and efficacy ingredients conventionally used for cosmetics and the like. Also, the agent of the present invention can be used in combination with the active ingredients generally used for external preparations, from the aspects of the effect thereof.

In the present specification, the "combined use" means use of the agent of the present invention before or simultaneously with or after the administration of the above-mentioned various ingredients, and also includes use of a mixture of the both as an additive. The administration form thereof is not limited as long as both the agent of the present invention and the above-mentioned various ingredients are used, and the effect of the above-mentioned various ingredients is enhanced.

EXAMPLES

The present invention is explained in more detail in the following by referring to Examples; however, the present invention is not limited by the following Examples.

1. Preparation of Protein-Glutaminase Solution and Transglutaminase Solution

A protein-glutaminase solution was prepared according to the method described in Y. Kikuchi et al., Applied microbiology and biotechnology 78, 67-74 (2008). That is, an expression plasmid was prepared by using a gene encoding a protein-glutaminase of *Chryseobacterium proteolyticum* (polynucleotide sequence shown in SEQ ID NO: 3), and introduced into *Corynebacterium glutamicum* to allow for secretory-expression of the protein-glutaminase, which was activated by protease, purified and dissolved in phosphate buffer.

A transglutaminase solution was prepared by purifying transglutaminase, obtained from a culture supernatant of *Streptomyces mobaraense*, according to the method described in K. Yokoyama et al., Protein Expression and Purification 26 329-335 (2002), and dissolving same in phosphate buffer.

2. Measurement of Swelling Degree

Hair was immobilized in a concave part of a glass slide for biochemical count having a depth of the concave part of 200 μm (manufactured by NIPPON Genetics Co, Ltd.), a cover glass was placed on the glass slide to cover the concave part, the diameter of the hair was measured 10-14 times, and the mean thereof was calculated ($D_0$). Thereafter, a sample was injected from the clearance between the cover glass and the glass slide, and left standing for 3 min or 5 min. The diameter of the hair was measured 10-14 times, and the mean was calculated ($D_1$).

As the sample, ion exchange water, phosphate buffer (pH 6.2), protein-glutaminase solution (6.2 mg/mL, pH 6.2) and 1% aqueous ammonia (pH 11.8) were used. The swelling degree was calculated from the measured diameters of the hair ($D_0$ and $D_1$) according to the following formula.

swelling degree (%)=100×($D_1$−$D_0$)/$D_0$

The results are shown in Table 1 and FIG. 1.

TABLE 1

|  | Example 1 | Comparative Example 1 | Comparative Example 2 | Comparative Example 3 |
|---|---|---|---|---|
| test solution | protein-glutaminase solution (6.2 mg/mL, pH 6.2) | ion exchange water | phosphate buffer (pH 6.2) | 1% aqueous ammonia (pH 11.8) |
| swelling degree (%) after 3 min | 10.4 | 9.4 | 6.3 | 11.1 |
| swelling degree (%) after 5 min | 11.1 | 8.9 | 6.2 | 11.3 |

From the results of Table 1 and FIG. 1, the swelling degree of the hair of Example 1 (protein-glutaminase solution) was higher than that of Comparative Example 1 (ion exchange water) and Comparative Example 2 (phosphate buffer) in both 3 min later and 5 min later, and of the same level as that of aqueous ammonia conventionally used as a hair swelling agent.

3. Observation of Hair Damage

Figure 2:
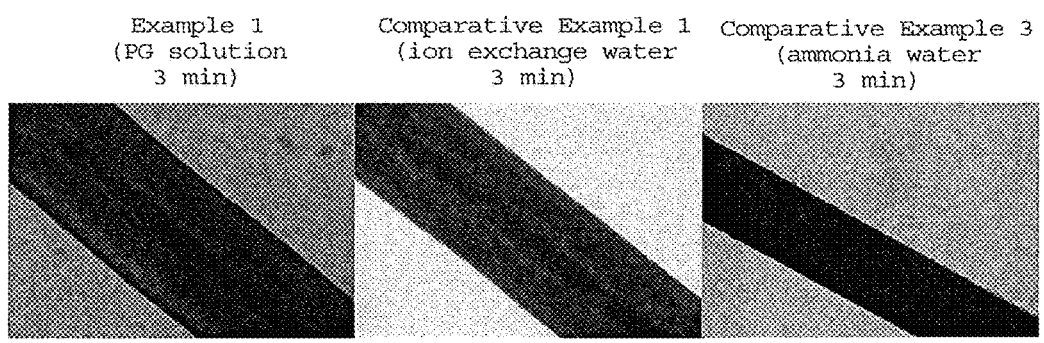
FIG. 2 show microscopic images (×400) of the condition of hair when treated for 3 min with various samples.

In the test of the above-mentioned 1, the condition of the hair 3 min after injection of ion exchange water, protein-glutaminase solution, or 1% aqueous ammonia was observed. Microscopic images of the hair subjected to various samples (magnification: ×400) are shown in FIG. 2.

As a result, cuticles on the hair surface were lifted when aqueous ammonia was used (Comparative Example 3). When protein-glutaminase was used (Example 1), the hair surface was not damaged at all, like the use of ion exchange water (Comparative Example 1).

From the results of the above-mentioned 1 and 2, it has been clarified that the protein-glutaminase effectively swells hair without damaging the hair.

4. Evaluation of Response of Protein-Glutaminase to Perm-Treated Hair

<1> Preparation of Perm-Treated Hair

Hair of Japanese women in their 20's was perm-treated and used as an experiment sample. The perm treatment included 1) immersing the hair in first perm liquid at 33° C. for 15 min and rinsing the first liquid with tap water at 35-40° C., and 2) immersing the hair in second perm liquid at 33° C. for 15 min and sufficiently rinsing same with tap water at 35-40° C. The continuous operation of 1) and 2) was repeated 4 times, and the hair was washed with 15% sodium laureth sulfate (EMAL E27C; Kao Corporation) and sufficiently rinsed with tap water at 35-40° C. The hair was immersed in a buffer, and treated with occasional stirring at room temperature for 10 min. The hair was combed out, hung while avoiding overlapped hair, and dried in a thermo-hygrostat room (23° C., 40% R.H.).

The first perm liquid, second perm liquid, and buffer used are as described below.

TABLE 2

| first perm liquid: ingredient name | amount (mass %) |
|---|---|
| ammonium thioglycolate (50%) | 14 |
| aqueous ammonia (28%) | 2 |
| monoethanolamine | 2 |
| purified water | balance |
| total | 100 |

TABLE 3

| second perm liquid: ingredient name | amount (mass %) |
|---|---|
| sodium bromate | 6 |
| purified water | 94 |
| total | 100 |

Buffer:
40 mM phosphoric acid, 40 mM acetic acid, 40 mM boric acid, sodium hydroxide, pH 4.5

<2> Quantification of Amount of Free Ammonia Produced

Using an Ammonia test kit (manufactured by Wako Pure Chemical Industries, Ltd.), the amount of free ammonia produced by reaction of protein-glutaminase with the above-mentioned perm-treated hair was quantified.

Figure 3:
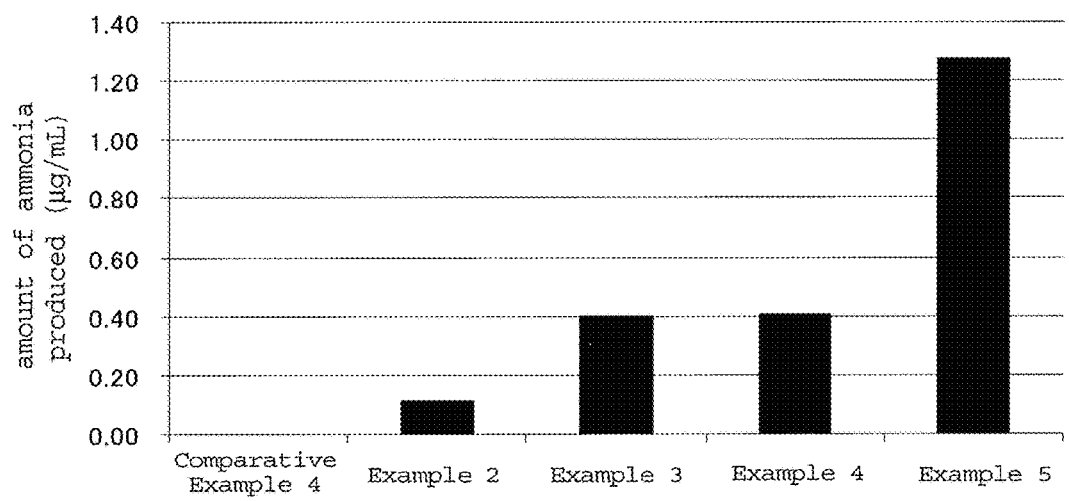
FIG. 3 is a graph showing the amount of ammonia production when treated with various samples. The vertical axis of the graph shows the amount of ammonia production (μg/mL), and the horizontal axis shows the kind of the samples.

The protein-glutaminase solution (2 ml) at a concentration shown in Table 4 was added to a bundle of the above-mentioned perm-treated hair (0.25 g), and the amount of ammonia in a sample after reaction at 37° C. for 1 hr was measured. The results are shown in Table 4 and FIG. 3. The amount of ammonia produced was shown as a value after subtraction of the amount of ammonia produced without addition of protein-glutaminase (Comparative Example 4).

TABLE 4

|  | Comparative Example 4 | Example 2 | Example 3 | Example 4 | Example 5 |
|---|---|---|---|---|---|
| protein-glutaminase solution (mg/ml) | 0.00 | 0.01 | 0.05 | 0.10 | 1.00 |
| amount of ammonia produced (ug/ml) | 0.00 | 0.12 | 0.40 | 0.40 | 1.28 |

From Table 4, protein-glutaminase reacted with perm-treated hair when the protein-glutaminase solution had a concentration of not less than 0.01 mg/ml.

5. Evaluation of Improved Permeability of Active Ingredient (Transglutaminase) to Hair by Protein-Glutaminase SOLUTION A (2 ml) shown in Table 5 was added to a bundle of the above-mentioned perm-treated hair (5 g), and the hair was wrapped with Saran Wrap (registered trade mark) (manufactured by Asahi Kasei Corporation) to allow for reaction at 37° C. for 30 min. After the reaction, the hair was washed twice by shaking in ultrapure water (30 sec each). Thereafter, SOLUTION B (2 ml) shown in Table 5 was added, and the hair was wrapped with Saran Wrap to allow for reaction at 37° C. for 30 min. After the reaction, the hair was washed twice by shaking in ultrapure water (30 sec each), and air-dried. The protein-glutaminase solution and transglutaminase solution used as SOLUTION A and SOLUTION B were adjusted to pH 6.0 with phosphate buffer.

Ten hairs were collected from each hair bundle after the reaction, and the long diameter and short diameter of each hair were measured by a laser micrometer (LS-7010MR: manufactured by Keyence Corporation). Thereafter, using a tensile tester (KES-G1: manufactured by Kato Tech Co., ltd.), the tensile strength of the hair was measured in pure water (measured length 40 mm). From the measurement values of the short diameter, long diameter and tensile strength, the strength of one hair with a long diameter of 80 µm and a short diameter of 80 µm was calculated, and the mean of the measurement results of 10 hairs was compared. The results are shown in Table 5.

TABLE 5

|  | Example 6 | Example 7 | Comparative Example 5 | Comparative Example 6 |
|---|---|---|---|---|
| SOLUTION A | protein-glutaminase solution (0.02 mg/ml) | protein-glutaminase solution (0.01 mg/ml) | phosphate buffer | phosphate buffer |
| SOLUTION B | transglutaminase solution (1 mg/ml) | transglutaminase solution (1 mg/ml) | phosphate buffer | transglutaminase solution (1 mg/ml) |
| pH | 6.0 | 6.0 | 6.0 | 6.0 |
| tensile strength (gf/p) | 18.2 | 18.4 | 13.2 | 15.8 |

As shown in Comparative Example 5 and Comparative Example 6, the tensile strength of the perm-treated hair increased from 13.2 (gf/p) to 15.8 (gf/p) by the application of transglutaminase. The results show that transglutaminase permeated to and reacted with the hair, and increased the strength. By comparison of Examples 6 and 7 with a treatment with protein-glutaminase in advance, and Comparative Example 6, the tensile strength increased from 15.8 (gf/p) to 18.2, 18.4 (gf/p). The results show that protein-glutaminase improves permeation level of transglutaminase, and the improved reactiveness of transglutaminase increases the strength.

From these results, it could be confirmed that protein-glutaminase improved permeability of transglutaminase, which is the active ingredient for hair strength, to the hair.

6. Evaluation of Improved Permeability of Active Ingredient (Hair Conditioner) to Hair by Protein-Glutaminase 1 g of hair (hair (normal hair) of Japanese women in their 20's and the above-mentioned perm-treated hair) was washed 3 times with 50 ml of phosphate buffer for 5 min. Then, each hair was immersed in 4 ml of protein-glutaminase solution (2 mg/ml) in Example 8 and Example 9, each hair was immersed in 4 ml of phosphate buffer in Comparative Example 7 and Comparative Example 8, and both were reacted at 37° C. for 30 min. Each hair after the reaction was washed 3 times with 50 ml of phosphate buffer for 5 min, washed with water and air dried.

0.5 g of hair conditioner ("Propoline" hair conditioner camomile & honey, manufactured by APIVITA) was applied to 1 g of hair for 30 sec, rinsed with tap water (running water) at 40° C. for 30 sec, and air dried in a thermo-hygrostat room (25° C., 40% R.H.).

The hair after drying was subjected to sensory evaluation of moist feeling, smoothness, absence of dry feeling of hair tip ends, and manageability of hair tip ends by five men and women by rating as follows.

<Moist Feeling>
2 points: strong moist feeling
1 point: moist feeling
0 point: no moist feeling
1 point: feel dry
<Smoothness>
2 point: very smooth
1 point: smooth
0 point: no smoothness
1 point: feel roughness
<Absence of Dry Feeling of Hair Tip Ends>
2 point: completely no dry feeling of hair tip ends
1 point: no dry feeling of hair tip ends
0 point: somewhat dry hair tip ends
−1 point: very dry feeling of hair tip ends
<Manageability of Hair Tip Ends>
2 point: very manageable hair tip ends
1 point: manageable hair tip ends
0 point: somewhat less manageability of hair tip ends
−1 point: completely no manageability of hair tip ends For evaluation, the grades of 5 panelists were totaled, 10-8 total points were marked with ⊙, 7-5 points were marked with ○, 4-0 points were marked with Δ, and −1--5 points were marked with x. The results are shown in Table 6.

TABLE 6

|  |  | Ex. 8 | Ex. 9 | Compar. Ex. 7 | Compar. Ex. 8 |
|---|---|---|---|---|---|
| evaluated hair | | normal hair | perm-treated hair | normal hair | perm-treated hair |
| | | protein glutaminase solution treatment | protein glutaminase solution treatment | phosphate buffer treatment | phosphate buffer treatment |
| sensory evaluation results | moist feeling | ⊙ | ⊙ | ○ | X |
| | smoothness | ⊙ | ⊙ | ○ | Δ |
| | absence of dry feeling of hair tip ends | ⊙ | ○ | X | X |

TABLE 6-continued

|  | Ex. 8 | Ex. 9 | Compar. Ex. 7 | Compar. Ex. 8 |
|---|---|---|---|---|
| manage-ability of hair tip ends | ⊙ | ○ | X | Δ |

As shown in Table 6, the hair treated with the protein-glutaminase solution (Example 8 and Example 9) was superior in moist feeling, smoothness, and manageability of hair tip ends of the hair after drying, and free of dry feeling as compared to the hair without a treatment with a protein-glutaminase solution (Comparative Example 7 and Comparative Example 8). These are the results of the treatment with a protein-glutaminase solution, which increased hydrophilicity of hair surface, increased adsorption of conditioning ingredients (stearamidopropyl dimethylamine, behentrimonium chloride, quaternium-80) and caused permeation of the active ingredient (panthenol) of the hair conditioner to the hair.

The components of the hair conditioner ("Propoline" hair conditioner camomile & honey, manufactured by APIVITA) used are as described below.

water, cetanol, stearamidopropyl dimethylamine, behentrimonium chloride, cetyl esters, quaternium-80, fragrance, citric acid, BG, ceteareth-12, benzyl alcohol, phenoxyethanol, panthenol, glycerin, potassium sorbate, hydrolyzed oats, tocopherol acetate, tocopherol, honey extract, camomilla recutita flower extract, gossypium herbaceum extract, rosmarumus officinalis leaf extract, butylphenyl methylpropanal, salvia officinalis leaf extract, hypericum perforatum flower/leaf/stem extract, coumarin, α-glucan oligosaccharide, Salvia sclarea oil, citrus aurantium dulcis peel oil

7. Evaluation of Improved Permeability of Active Ingredient (Peptide) to Skin by Protein-Glutaminase Using glycylglycylglycine (hereinafter indicated as "Gly-Gly-Gly") (manufactured by PEPTIDE INSTITUTE, INC.) as a peptide to be evaluated for skin permeability, the permeability of Gly-Gly-Gly to commercially available artificial cultured skin (3D cultured human skin model: TESTSKIN LSE-high, manufactured by Toyobo Co., Ltd.) was evaluated. Gly-Gly-Gly was labeled with fluorescein by using fluorescein isothiocyanate (FITC-I, manufactured by Chemical-Dojin Co., Ltd.) to enable highly sensitive detection.

The cultured skin is cultured on a polycarbonate membrane on the bottom of a transwell, and set on a 6-well assay plate. Phosphate buffer (−) (1.2 ml) was added to the assay plate to soak the bottom part (corium side) of the cultured skin. An assay ring was mounted on the top (corneum side) of the cultured skin, FITC-labeled Gly-Gly-Gly sample was added and incubated for a given time period. The permeability was evaluated by measuring the amount of FITC-labeled Gly-Gly-Gly that permeated the cultured skin to move into phosphate buffer (−).

First, a protein-glutaminase solution (4 mg/ml, 100 μl) was added to the top of the cultured skin and incubated at 37° C. for 30 min, after which a FITC-labeled Gly-Gly-Gly sample (100 μl) was added to the top of the cultured skin. After 2, 5, and 20 hr, the amount of FITC-labeled Gly-Gly-Gly that permeated the cultured skin and moved into phosphate buffer (−) was measured. As a comparison target, phosphate buffer (−) was added to the top of the cultured skin instead of a protein-glutaminase solution. The fluorescence intensity was measured under the conditions of exciting wavelength 492 nm and fluorescence wavelength 520 nm. The fluorescence intensity was measured using platereader SpectraMaxM2 (manufactured by Molecular Devices, LLC.). The results thereof are shown in FIG. 4.

Figure 4:
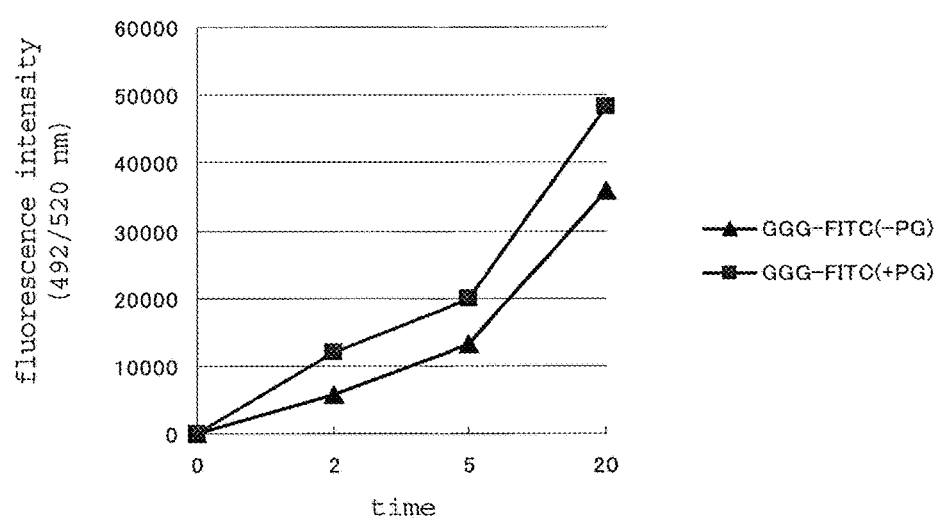
FIG. 4 is a graph showing the amount of the active ingredient that permeated to the cultured skin. In the graph, the vertical axis shows fluorescence intensity of the fluorescein-labeled active ingredient, and the horizontal axis shows the time (min) after addition of the active ingredient to cultured skin. In addition, "GGG-FITC(-PG)" shows the fluorescence intensity when a protein-glutaminase was not used, and "GGG-FITC(+PG)" shows the fluorescence intensity when a protein-glutaminase was used.

As shown in FIG. 4, it was clarified that a treatment of cultured skin with protein-glutaminase improved permeability of peptide more than when untreated cultured skin was used. The results suggest that human skin reacted with protein-glutaminase shows enhanced hydrophilicity of corneum, and improved permeability of hydrophilic substances such as amino acid, peptide and the like to the skin. Since amino acid, peptide and the like (including the aforementioned acylamino acid, acylpeptide and derivatives thereof) can be an active ingredient for the skin and hair depending on the kind, use thereof in combination with protein-glutaminase is considered to be extremely useful for the skin and hair.

8. Formulation Examples 1-5

The permanent wave pretreatment agent (Formulation Example 1), reducing agent for permanent wave product (Formulation Example 2), oxidative hair dye (Formulation Example 3), color rinse (Formulation Example 4) and gel-like whitening serum (Formulation Example 5) prepared with the formulations shown in the following Table according to a conventional method are useful for increasing the hydrophilicity of protein contained in the hair, skin and the like. The amount of each ingredient described in each Table (numerical values in Tables) is in mass fraction (%) based on the whole formulation as 100.

TABLE 7

Formulation Example 1: permanent wave pretreatment agent

| ingredient | amount (mass %) |
|---|---|
| amino acid mixture PRODEW (registered trade mark) 500 (manufactured by Ajinomoto Co., Inc.) | 10.0 |
| protein-glutaminase | 10.0 |
| phosphate buffer (pH 6) | 10.0 |
| cetrimonium chloride | 1.0 |
| ethanol | 3.0 |
| water | balance |
| total | 100.0 |

TABLE 8

Formulation Example 2: reducing agent for permanent wave product

| ingredient | amount (mass %) |
|---|---|
| 50% ammonium thioglycolate | 9.0 |
| 40% diammonium dithiodiglycolate | 2.0 |

TABLE 8-continued

Formulation Example 2: reducing agent for permanent wave product

| ingredient | amount (mass %) |
|---|---|
| protein-glutaminase | 5.0 |
| phosphate buffer (pH 6) | 10.0 |
| PEG-20 sorbitan cocoate | 1.0 |
| EDTA | 0.1 |
| water | balance |
| total | 100.0 |

TABLE 9

Formulation Example 3: oxidative hair dye

| ingredient | amount (mass %) |
|---|---|
| <first agent> | |
| glyceryl monooleate | 1.0 |
| isopropyl myristate | 2.5 |
| octyldodecanol | 0.2 |
| cetyl alcohol | 14.0 |
| laureth-25 | 1.8 |
| ceteth-40 | 2.0 |
| 30% TEA-cocoyl glutamate | 0.8 |
| cocamide DEA | 0.2 |
| p-phenylenediamine | 1.2 |
| resorcin | 0.5 |
| m-aminophenol | 0.3 |
| sodium sulfite | 1.2 |
| water | balance |
| Total | 100.0 |
| <second agent> | |
| 35% hydrogen peroxide water | 16.9 |
| 60% hydroxyethane diphosphonic acid | 0.17 |
| protein-glutaminase | 5.0 |
| phosphate buffer (pH 6) | 5.0 |
| water | balance |
| total | 100.0 |

TABLE 10

Formulation Example 4: color rinse

| ingredient | amount (mass %) |
|---|---|
| 35% hydrogen peroxide water | 10.0 |
| sodium PCA | 0.1 |
| sodium dilauramidoglutamide lysine | 0.1 |
| phytosteryl/octyldodecyl lauroyl glutamate | 0.05 |
| hydroxyethane diphosphonic acid | 0.1 |
| hydroxyethyl cellulose | 3.0 |
| propylene glycol | 5.0 |
| tocopherol acetate | 0.5 |
| ethanol | 5.0 |
| benzyl alcohol | 5.0 |

TABLE 10-continued

Formulation Example 4: color rinse

| ingredient | amount (mass %) |
|---|---|
| red No. 201 | 0.1 |
| violet No. 402 | 0.1 |
| protein-glutaminase | 3.0 |
| citric acid | appropriate (pH 4.0) |
| water | balance |
| total | 100.0 |

TABLE 11

Formulation Example 5: gel-like whitening serum

| ingredient | amount (mass %) |
|---|---|
| macadamia nut oil | 5.0 |
| squalane | 5.0 |
| behenyl alcohol | 3.0 |
| phytosteryl/octyldodecyl lauroyl glutamate | 0.5 |
| polyglyceryl-10 tristearate | 1.5 |
| glyceryl stearate | 0.5 |
| Lauroyllysine | 0.1 |
| vitamin E | 0.2 |
| dimethicone | 5.0 |
| hydrogenated lecithin | 0.2 |
| glycerin | 14.0 |
| BG | 4.0 |
| Carbomer | 0.4 |
| 3-O-ethylascorbic acid | 0.1 |
| Disodium EDTA | 0.05 |
| pentagalloyl glucoside | 0.1 |
| PRODEW (registered trade mark) 400 (manufactured by Ajinomoto Co., Inc.) | 0.1 |
| PCA ethyl cocoyl arginate | 0.01 |
| protein-glutaminase | 1.0 |
| preservative | appropriately |
| water | balance |
| total | 100.0 |

INDUSTRIAL APPLICABILITY

According to the present invention, a cosmetic useful for increasing hydrophilicity of the protein contained in hair, skin and the like can be provided. Particularly, according to the present invention, hair can be effectively swollen without damaging the hair, and hair strength can be effectively improved. Therefore, a hair cosmetic useful for, for example, perming agents, hair colors and the like can be provided. According to the present invention, moreover, an agent that effectively increases hydrophilicity of protein can be provided, as well as an agent that enhances permeation of an active ingredient to a tissue can also be provided. These agents are useful not only as cosmetics but also in the pharmaceutical field.

This application is based on patent application No. 2012-229590 filed in Japan (filing date: Oct. 17, 2012), the contents of which are encompassed in full herein.

The invention claimed is:

1. A method for perming or coloring hair, comprising:
 treating hair with a cosmetic composition,
 wherein the cosmetic composition comprises a protein-glutaminase, and the cosmetic composition is free of an alkaline substance and is free of a transglutaminase.

2. The method of claim 1, wherein the cosmetic composition further comprises at least one of a hair perm agent and a hair coloring agent.

3. The method of claim 1, wherein the protein-glutaminase has a molecular weight of 10 kDa to 40 kDa.

4. The method of claim 1, wherein the protein-glutaminase is derived from a bacterium belonging to the genus *Chryseobacterium*.

5. The method of claim 1, wherein the cosmetic composition further comprises a further component selected from the group consisting of an amino acid, an acylamino acid, an acylamino acid ester, an acylamino acid amide, a peptide, an acylpeptide, a salt thereof, and a combination thereof.

6. The method of claim 5, wherein the cosmetic composition comprises 0.005 to 50 mass % of the further component, based on the total mass of the cosmetic composition.

7. The method of claim 1, wherein the cosmetic composition further comprises an alcohol.

8. The method of claim 7, wherein the cosmetic composition comprises 0.005 to 50 mass % of the alcohol, based on the total mass of the cosmetic composition.

9. The method of claim 7, wherein the alcohol is a saturated or unsaturated monovalent $C_{1-6}$ alcohol or a polyvalent alcohol.

10. The method of claim 1, wherein the cosmetic composition further comprises a hair coloring agent.

11. The method of claim 10, wherein the hair coloring agent comprises p-phenylenediamine.

12. The method of claim 1, wherein the hair is treated with the cosmetic composition to perm the hair.

13. The method of claim 1, wherein the hair is treated with the cosmetic composition to change the color the hair.

14. A method of enhancing hair-permeation of an active ingredient included in a cosmetic composition, comprising:
 including a protein-glutaminase in the cosmetic composition,
 wherein the cosmetic composition is free of an alkaline substance and is free of a transglutaminase, and
 the active ingredient is at least one of a hair perm agent and a hair coloring agent.

15. A method for treating human hair, comprising:
 perming the human hair with a first perm composition comprising ammonium thioglycolate and at least one of aqueous ammonia and monoethanolamine and a second perm composition comprising sodium bromate;
 applying to the permed hair a first composition comprising protein-glutaminase and not comprising an alkaline substance; and then
 applying to the permed hair a second composition comprising transglutaminase,
 wherein the first and second compositions applied to the permed hair are different.

16. The method of claim 15, wherein the first composition applied to the permed hair comprises 0.00001 to 10 mass % of the protein-glutaminase, based on the total mass of the first composition applied to the permed hair.

17. The method of claim 15, wherein the second composition applied to the permed hair comprises 0.001 to 2 mass % of the transglutaminase, based on the total mass of the second composition applied to the permed hair.

18. The method of claim 15, wherein the first and second compositions are applied to the permed hair such that a mass ratio of the protein-glutaminase to the transglutaminase applied to the permed hair is from 1:1 to 1:10000.

19. The method of claim 15, wherein the protein-glutaminase has a molecular weight of 10 kDa to 40 kDa.

20. The method of claim 15, wherein the protein-glutaminase is derived from a bacterium belonging to the genus *Chryseobacterium*.

* * * * *

SEQUENCE LISTING

<160> NUMBER OF SEQ ID NOS: 4

<210> SEQ ID NO 1
<211> LENGTH: 1380

<212> TYPE: DNA
<213> ORGANISM: Chryseobacterium proteolyticum
<220> FEATURE:
<221> NAME/KEY: CDS
<222> LOCATION: (181)..(1143)

<400> SEQUENCE: 1

```
gtagttttta atgaacaaaa cactttaatt attactaaaa attttggttt ttataaaaat    60
aacttgctta tgttattttt tttattaatt ttatttcac  caaaaagtga agtaaataaa   120
agttaaaata accaaccaac ttaacaaaaa ctcaccatta aactacaaat tacaattatt   180
```

| | | | | | | | | | | | | | | | | |
|---|---|---|---|---|---|---|---|---|---|---|---|---|---|---|---|---|
| atg | aaa | aat | ctt | ttt | tta | tca | atg | atg | gcc | ttt | gtg | acc | gtc | tta | act | 228 |
| Met | Lys | Asn | Leu | Phe | Leu | Ser | Met | Met | Ala | Phe | Val | Thr | Val | Leu | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | aat | tcc | tgt | gcc | gat | tcc | aac | ggg | aat | cag | gaa | atc | aac | gga | aag | 276 |
| Phe | Asn | Ser | Cys | Ala | Asp | Ser | Asn | Gly | Asn | Gln | Glu | Ile | Asn | Gly | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| gaa | aaa | cta | agt | gta | aat | gat | tct | aag | ctg | aaa | gat | ttc | gga | aag | act | 324 |
| Glu | Lys | Leu | Ser | Val | Asn | Asp | Ser | Lys | Leu | Lys | Asp | Phe | Gly | Lys | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| gta | ccg | gta | ggg | ata | gac | gaa | gaa | aac | gga | atg | ata | aag | gtg | tca | ttt | 372 |
| Val | Pro | Val | Gly | Ile | Asp | Glu | Glu | Asn | Gly | Met | Ile | Lys | Val | Ser | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| atg | tta | act | gcg | caa | ttc | tat | gaa | att | aag | ccg | acc | aaa | gaa | aat | gag | 420 |
| Met | Leu | Thr | Ala | Gln | Phe | Tyr | Glu | Ile | Lys | Pro | Thr | Lys | Glu | Asn | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cag | tat | atc | gga | atg | ctt | aga | cag | gct | gtt | aag | aat | gaa | tct | cct | gta | 468 |
| Gln | Tyr | Ile | Gly | Met | Leu | Arg | Gln | Ala | Val | Lys | Asn | Glu | Ser | Pro | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| cac | att | ttc | tta | aag | cct | aat | agc | aat | gaa | ata | gga | aaa | gtg | gag | tct | 516 |
| His | Ile | Phe | Leu | Lys | Pro | Asn | Ser | Asn | Glu | Ile | Gly | Lys | Val | Glu | Ser | |
| | | | | 100 | | | | | 105 | | | | | 110 | | |

| | | | | | | | | | | | | | | | | |
|---|---|---|---|---|---|---|---|---|---|---|---|---|---|---|---|---|
| gca | agt | ccg | gaa | gac | gta | aga | tat | ttt | aaa | acg | atc | ctg | aca | aaa | gaa | 564 |
| Ala | Ser | Pro | Glu | Asp | Val | Arg | Tyr | Phe | Lys | Thr | Ile | Leu | Thr | Lys | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| gta | aaa | ggg | caa | acc | aat | aaa | ttg | gcg | agt | gta | att | cct | gat | gta | gct | 612 |
| Val | Lys | Gly | Gln | Thr | Asn | Lys | Leu | Ala | Ser | Val | Ile | Pro | Asp | Val | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| aca | tta | aat | tct | tta | ttc | aat | caa | ata | aag | aat | cag | tct | tgc | ggt | acc | 660 |
| Thr | Leu | Asn | Ser | Leu | Phe | Asn | Gln | Ile | Lys | Asn | Gln | Ser | Cys | Gly | Thr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tct | acg | gcg | tcc | tca | cca | tgc | atc | aca | ttc | aga | tat | cct | gta | gac | gga | 708 |
| Ser | Thr | Ala | Ser | Ser | Pro | Cys | Ile | Thr | Phe | Arg | Tyr | Pro | Val | Asp | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| tgt | tat | gca | aga | gcc | cat | aag | atg | aga | caa | atc | tta | atg | aac | aac | ggc | 756 |
| Cys | Tyr | Ala | Arg | Ala | His | Lys | Met | Arg | Gln | Ile | Leu | Met | Asn | Asn | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| tat | gac | tgt | gaa | aaa | caa | ttt | gta | tac | gga | aac | cta | aag | gca | tca | aca | 804 |
| Tyr | Asp | Cys | Glu | Lys | Gln | Phe | Val | Tyr | Gly | Asn | Leu | Lys | Ala | Ser | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| gga | act | tgc | tgt | gtg | gcg | tgg | agc | tac | cac | gtt | gca | ata | ttg | gta | agc | 852 |
| Gly | Thr | Cys | Cys | Val | Ala | Trp | Ser | Tyr | His | Val | Ala | Ile | Leu | Val | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | aaa | aat | gct | tcc | gga | gta | acg | gaa | aaa | aga | att | att | gat | cct | tca | 900 |
| Tyr | Lys | Asn | Ala | Ser | Gly | Val | Thr | Glu | Lys | Arg | Ile | Ile | Asp | Pro | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cta | ttt | tca | agc | ggt | cct | gta | aca | gat | aca | gca | tgg | aga | aac | gct | tgc | 948 |
| Leu | Phe | Ser | Ser | Gly | Pro | Val | Thr | Asp | Thr | Ala | Trp | Arg | Asn | Ala | Cys | |
| | | | | 245 | | | | | 250 | | | | | 255 | | |

| | | | | | | | | | | | | | | | | |
|---|---|---|---|---|---|---|---|---|---|---|---|---|---|---|---|---|
| gtt | aac | acc | tct | tgc | gga | tct | gca | tcc | gtt | tcc | tct | tat | gct | aat | act | 996 |

```
                Val Asn Thr Ser Cys Gly Ser Ala Ser Val Ser Ser Tyr Ala Asn Thr
                            260                 265                 270 gca gga aat gtt tat tac aga agt cct agt aat tct tac ctg tat gac         1044
Ala Gly Asn Val Tyr Tyr Arg Ser Pro Ser Asn Ser Tyr Leu Tyr Asp
            275                 280                 285 aac aat ctg atc aat acc aac tgt gta ctg act aaa ttt tca ctg ctt         1092
Asn Asn Leu Ile Asn Thr Asn Cys Val Leu Thr Lys Phe Ser Leu Leu
        290                 295                 300 tcc gga tgt tct cct tca cct gca ccg gat gta tcc agc tgt gga ttt         1140
Ser Gly Cys Ser Pro Ser Pro Ala Pro Asp Val Ser Ser Cys Gly Phe
305                 310                 315                 320 taa ttaattgata attttacagc acctgctcat ttacagaatc agcaggtgct              1193
gttatataat aatactattt ttatgaaagt atggacatta ctattatttt tttgtatgat       1253
aacatcctgc tccggtagtt cgggttcaca gaatttaacc tggtacaaaa atgcaacaat       1313
cagtcagatt acggaagacc ccgatcatcc cggggatttt atgcgtatct ctattggaat       1373
cagcgcg                                                                 1380

<210> SEQ ID NO 2
<211> LENGTH: 320
<212> TYPE: PRT
<213> ORGANISM: Chryseobacterium proteolyticum

<400> SEQUENCE: 2

Met Lys Asn Leu Phe Leu Ser Met Met Ala Phe Val Thr Val Leu Thr
1               5                   10                  15

Phe Asn Ser Cys Ala Asp Ser Asn Gly Asn Gln Glu Ile Asn Gly Lys
            20                  25                  30

Glu Lys Leu Ser Val Asn Asp Ser Lys Leu Lys Asp Phe Gly Lys Thr
        35                  40                  45

Val Pro Val Gly Ile Asp Glu Glu Asn Gly Met Ile Lys Val Ser Phe
    50                  55                  60

Met Leu Thr Ala Gln Phe Tyr Glu Ile Lys Pro Thr Lys Glu Asn Glu
65                  70                  75                  80

Gln Tyr Ile Gly Met Leu Arg Gln Ala Val Lys Asn Glu Ser Pro Val
                85                  90                  95

His Ile Phe Leu Lys Pro Asn Ser Asn Glu Ile Gly Lys Val Glu Ser
            100                 105                 110

Ala Ser Pro Glu Asp Val Arg Tyr Phe Lys Thr Ile Leu Thr Lys Glu
        115                 120                 125

Val Lys Gly Gln Thr Asn Lys Leu Ala Ser Val Ile Pro Asp Val Ala
    130                 135                 140

Thr Leu Asn Ser Leu Phe Asn Gln Ile Lys Asn Gln Ser Cys Gly Thr
145                 150                 155                 160

Ser Thr Ala Ser Ser Pro Cys Ile Thr Phe Arg Tyr Pro Val Asp Gly
                165                 170                 175

Cys Tyr Ala Arg Ala His Lys Met Arg Gln Ile Leu Met Asn Asn Gly
            180                 185                 190

Tyr Asp Cys Glu Lys Gln Phe Val Tyr Gly Asn Leu Lys Ala Ser Thr
        195                 200                 205

Gly Thr Cys Cys Val Ala Trp Ser Tyr His Val Ala Ile Leu Val Ser
    210                 215                 220

Tyr Lys Asn Ala Ser Gly Val Thr Glu Lys Arg Ile Ile Asp Pro Ser
225                 230                 235                 240

Leu Phe Ser Ser Gly Pro Val Thr Asp Thr Ala Trp Arg Asn Ala Cys
```

-continued

```
                    245                 250                 255
Val Asn Thr Ser Cys Gly Ser Ala Ser Val Ser Ser Tyr Ala Asn Thr
                260                 265                 270

Ala Gly Asn Val Tyr Tyr Arg Ser Pro Ser Asn Ser Tyr Leu Tyr Asp
            275                 280                 285

Asn Asn Leu Ile Asn Thr Asn Cys Val Leu Thr Lys Phe Ser Leu Leu
    290                 295                 300

Ser Gly Cys Ser Pro Ser Pro Ala Pro Asp Val Ser Ser Cys Gly Phe
305                 310                 315                 320

<210> SEQ ID NO 3
<211> LENGTH: 555
<212> TYPE: DNA
<213> ORGANISM: Chryseobacterium proteolyticum
<220> FEATURE:
<221> NAME/KEY: CDS
<222> LOCATION: (1)..(555)

<400> SEQUENCE: 3 ttg gcg agt gta att cct gat gta gct aca tta aat tct tta ttc aat      48
Leu Ala Ser Val Ile Pro Asp Val Ala Thr Leu Asn Ser Leu Phe Asn
1               5                   10                  15 caa ata aag aat cag tct tgc ggt acc tct acg gcg tcc tca cca tgc      96
Gln Ile Lys Asn Gln Ser Cys Gly Thr Ser Thr Ala Ser Ser Pro Cys
            20                  25                  30 atc aca ttc aga tat cct gta gac gga tgt tat gca aga gcc cat aag     144
Ile Thr Phe Arg Tyr Pro Val Asp Gly Cys Tyr Ala Arg Ala His Lys
        35                  40                  45 atg aga caa atc tta atg aac aac ggc tat gac tgt gaa aaa caa ttt     192
Met Arg Gln Ile Leu Met Asn Asn Gly Tyr Asp Cys Glu Lys Gln Phe
    50                  55                  60 gta tac gga aac cta aag gca tca aca gga act tgc tgt gtg gcg tgg     240
Val Tyr Gly Asn Leu Lys Ala Ser Thr Gly Thr Cys Cys Val Ala Trp
65                  70                  75                  80 agc tac cac gtt gca ata ttg gta agc tat aaa aat gct tcc gga gta     288
Ser Tyr His Val Ala Ile Leu Val Ser Tyr Lys Asn Ala Ser Gly Val
                85                  90                  95 acg gaa aaa aga att att gat cct tca cta ttt tca agc ggt cct gta     336
Thr Glu Lys Arg Ile Ile Asp Pro Ser Leu Phe Ser Ser Gly Pro Val
            100                 105                 110 aca gat aca gca tgg aga aac gct tgc gtt aac acc tct tgc gga tct     384
Thr Asp Thr Ala Trp Arg Asn Ala Cys Val Asn Thr Ser Cys Gly Ser
        115                 120                 125 gca tcc gtt tcc tct tat gct aat act gca gga aat gtt tat tac aga     432
Ala Ser Val Ser Ser Tyr Ala Asn Thr Ala Gly Asn Val Tyr Tyr Arg
    130                 135                 140 agt cct agt aat tct tac ctg tat gac aac aat ctg atc aat acc aac     480
Ser Pro Ser Asn Ser Tyr Leu Tyr Asp Asn Asn Leu Ile Asn Thr Asn
145                 150                 155                 160 tgt gta ctg act aaa ttt tca ctg ctt tcc gga tgt tct cct tca cct     528
Cys Val Leu Thr Lys Phe Ser Leu Leu Ser Gly Cys Ser Pro Ser Pro
                165                 170                 175 gca ccg gat gta tcc agc tgt gga ttt                                 555
Ala Pro Asp Val Ser Ser Cys Gly Phe
            180                 185

<210> SEQ ID NO 4
<211> LENGTH: 185
<212> TYPE: PRT
<213> ORGANISM: Chryseobacterium proteolyticum
```

-continued

```
<400> SEQUENCE: 4

Leu Ala Ser Val Ile Pro Asp Val Ala Thr Leu Asn Ser Leu Phe Asn
1               5                   10                  15

Gln Ile Lys Asn Gln Ser Cys Gly Thr Ser Thr Ala Ser Ser Pro Cys
            20                  25                  30

Ile Thr Phe Arg Tyr Pro Val Asp Gly Cys Tyr Ala Arg Ala His Lys
        35                  40                  45

Met Arg Gln Ile Leu Met Asn Asn Gly Tyr Asp Cys Glu Lys Gln Phe
    50                  55                  60

Val Tyr Gly Asn Leu Lys Ala Ser Thr Gly Thr Cys Cys Val Ala Trp
65                  70                  75                  80

Ser Tyr His Val Ala Ile Leu Val Ser Tyr Lys Asn Ala Ser Gly Val
                85                  90                  95

Thr Glu Lys Arg Ile Ile Asp Pro Ser Leu Phe Ser Ser Gly Pro Val
            100                 105                 110

Thr Asp Thr Ala Trp Arg Asn Ala Cys Val Asn Thr Ser Cys Gly Ser
        115                 120                 125

Ala Ser Val Ser Ser Tyr Ala Asn Thr Ala Gly Asn Val Tyr Tyr Arg
    130                 135                 140

Ser Pro Ser Asn Ser Tyr Leu Tyr Asp Asn Asn Leu Ile Asn Thr Asn
145                 150                 155                 160

Cys Val Leu Thr Lys Phe Ser Leu Leu Ser Gly Cys Ser Pro Ser Pro
            165                 170                 175

Ala Pro Asp Val Ser Ser Cys Gly Phe
            180                 185
```